United States Patent [19]

Budai et al.

[11] Patent Number: 4,621,101

[45] Date of Patent: Nov. 4, 1986

[54] PHARMACEUTICAL COMPOSITIONS WITH ANTIANGINAL ACTIVITY

[75] Inventors: Zoltán Budai; Tibor Mezei; Aranka Lay nee Konya; Lujza Petocz; Katalin Grasser; Zsuzsanna Orr, all of Budapest, Hungary

[73] Assignee: Egis Gyogyszergyar, Budapest, Hungary

[21] Appl. No.: 751,623

[22] Filed: Jul. 2, 1985

[30] Foreign Application Priority Data

Jul. 10, 1984 [HU] Hungary .............................. 2679/84

[51] Int. Cl.$^4$ ............................................. A61K 31/15
[52] U.S. Cl. .................................................... 514/640
[58] Field of Search .......................................... 514/640

[56] References Cited

U.S. PATENT DOCUMENTS 4,077,999 3/1978 Budai et al. ........................ 514/640
4,395,413 7/1983 Budai et al. ........................ 564/256

OTHER PUBLICATIONS

Chem. Abst. 92: 163620r (1980).
Chem. Abst. 96: 46032x (1982)—Ruediger et al.
AMA Drug Evaluations, pp. 662-664 and 624-625.

*Primary Examiner*—Douglas W. Robinson
*Attorney, Agent, or Firm*—Karl F. Ross; Herbert Dubno

[57] ABSTRACT

The invention relates to pharmaceutical compositions possessing valuable antianginal activity. These compositions show higher activity and more favorable therapeutic indices than the reference compound Prenylamine. Preparation of different kinds of pharmaceutical compositions, such as tablets, dragées, capsules and injectable solutions, containing compounds of general formula (I)

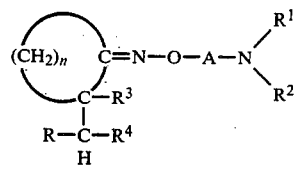

or their acid addition salts as active ingredients, is disclosed, wherein in formula (I)

R is phenyl or 4-chlorophenyl;
$R^1$ and $R^2$ each represent hydrogen, methyl or isopropyl;
$R^3$ and $R^4$ are hydrogen, or together form a chemical bond;
n is an integer from 4 to 6;
A means trimethylene, if n is 4 or 6; or ethylene, if n is 5.

6 Claims, No Drawings

PHARMACEUTICAL COMPOSITIONS WITH ANTIANGINAL ACTIVITY

FIELD OF THE INVENTION

The Invention relates to pharmaceutical compositions containing basic oxime ethers having antianginal activity, their use in the therapy and a process for their preparation.

BACKGROUND OF THE INVENTION

It is known from Hungarian patent specification No. 169,298 that the basic oxime ethers of formula (IX)

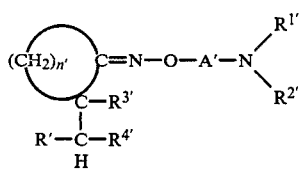
(IX)

possess antidepressant, antiparkinsonic and local anaesthetic activities; in formula (IX)

R' stands for phenyl, optionally substituted by Hal, or one or more hydroxy, nitro or $C_{1-4}$ alkoxy groups(s), $R^{3'}$ and $R^{4'}$ each represents hydrogen, or together they form a chemical bond;

A' is a straight or branched chain alkylene group having 2 to 4 carbon atoms;

$R^{1'}$ and $R^{2'}$ each is hydrogen or $C_{1-4}$ alkyl, or together they form an alkylene group consisting of 4 to 7 carbon atoms being optionally interrupted by a heteroatom, namely an oxygen or nitrogen atom, the latter being optionally substituted by a benzyl or a $C_{1-3}$ alkyl group;

n' is an integer from 3 to 7.

DESCRIPTION OF THE INVENTION

It has now been found that compounds of the general formula (I)

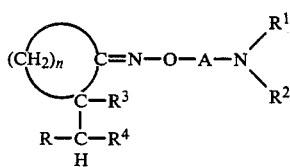
(I)

which fall within the above mentioned formula (IX) but have not been specifically disclosed therein, have valuable therapeutical, namely antianginal properties, and thus are suitable for use in pharmaceutical compositions.

The invention therefore provides pharmaceutical compositions with antianginal activity containing as active agent a compound of the general formula (I). In respect of the preparation of the compounds of general formula (I) only the present disclosure refers to the mentioned Hungarian patent specification No. 169,298 which describes the following process variants (a) to (d):

(a) reacting a ketone or thione of formula (II)

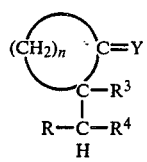
(II)

with a hydroxylamine derivative of formula (III)

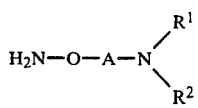
(III)

or an acid addition salt thereof;
(b) reacting a chloro compound of formula (IV)

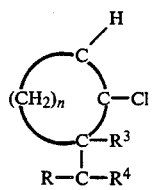
(IV)

with a hydroxylamine derivative of formula (III) or an acid addition salt thereof;
(c) reacting an oxime of the formula (V)

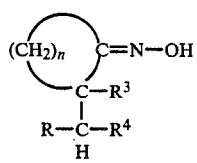
(V)

with a haloalkyl amine derivative of the formula (VI)

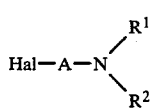
(VI)

in an inert solvent medium, in the presence of a basic condensing agent;
(d) reacting an oxime of formula (V) with a dihalo alkane of formula (VII)

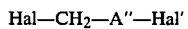
Hal—CH$_2$—A''—Hal' (VII)

and aminating the haloalkyl ether thus obtained with an amine of the formula (VIII).

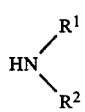
(VIII)

The compounds of the formula (I) obtained by one of the above routes may—if desired—be converted into their acid addition salts by using a pharmaceutically acceptable acid. The compounds of the formula (I) and their acid addition salts can be formulated to pharmaceutical compositions by methods known per se.

In the above formulae if n=4, then (A₁)
R³ and R⁴ together form a chemical bond,
R is phenyl,
A means trimethylene,
R¹ and R² represent a methyl group each, and the molecule has an (E,Z) configuration; or (A₂)
R³ and R⁴ together form a chemical bond,
R means 4-chlorophenyl,
A is ethylene,
R¹ is isopropyl,
R² is hydrogen, and the molecule has an (E,E) configuration; or (A₃)
R³ and R⁴ together form a chemical bond,
R is 4-chlorophenyl,
A is trimethylene,
R¹ and R² represent an isopropyl group each, and the molecule has an (E,E) configuration; or (A₄)
R³ and R⁴ together form a chemical bond,
R means phenyl,
A₁ is trimethylene,
R¹ and R² represent an isopropyl group each, and the molecule has an (E,E) configuration; or (A₅)
R³ and R⁴ together form a chemical bond,
R is phenyl,
A means ethylene,
R¹ stands for isopropyl,
R² is hydrogen, and the molecule has an (E,E) configuration; or (A₆)
R³ and R⁴ together form a chemical bond,
R means phenyl,
A is ethylene,
R¹ and R² stand for an isopropyl group each, and the molecule has an (E,E) configuration; or if n=5, then (B₁)
R³ and R⁴ together form a chemical bond,
R is phenyl,
A is ethylene,
R¹ and R² represent a methyl group each, and the molecule has a (Z,E) configuration; or (B₂)
R³ and R⁴ stand for hydrogen each,
R means phenyl,
A is ethylene,
R¹ and R² stand for a methyl group each, and the molecules has an (E,E) configuration; or (B₃)
R³ and R⁴ together form a chemical bond,
R is phenyl,
A stands for ethylene,
R¹ and R² represent a methyl group each, and the molecule has an (E,E) configuration; or (B₄)
R³ and R⁴ together form a chemical bond,
R means phenyl,
A is ethylene,
R¹ and R² represent an isopropyl group each, and the molecule has a (Z,E) configuration; or if n=6, then (C)
R³ and R⁴ together form a chemical bond,
R is phenyl,
A stands for trimethylene,
R¹ and R² represent a methyl group each, and the molecules has an (E,E) configuration.

Further, in the above formulae (I) to (VIII)
Y stands for an oxygen or a sulfur atom;
Hal means halogen;
A' represents an alkylene containing one less methylene than A does;
Hal' represents a halogen that may be identical with or different from the halogen represented by Hal.

The following compounds of the formula (I) or pharmaceutically acceptable acid addition salts thereof can be prepared by the method described in said Hungarian patent specification and can preferably be used as active ingredients in pharmaceutical compositions according to the present invention:

2-(E)-phenylmethylene]-1-[(Z)-(3-dimethylaminopropyloxyimino)]-cyclohexane (compound A);

2-[(Z)-phenylmethylene]-1-[(E)-(2-dimethylaminoethoxyimino)]-cycloheptane (compound B);

2-[(E)-(4-chlorophenyl)-methylene]-1-[(E)-(2-isopropylamino-ethoxyimino)]-cyclohexane (compound C);

2-benzyl-1-[(E)-(2-dimethylamino-ethoxyimino)]-cycloheptane (compound D);

2-[(E)-phenylmethylene]-1-[(E)-(2-dimethylaminoethoxyimino)]-cycloheptane (compound E);

2-[(E)-(4-chlorophenyl)-methylene]-1-[(E)-(3-diisopropylamino)-propyloxyimino]-cyclohexane (compound F);

2-[(E)-phenylmethylene]-1-[(E)-(3-diisopropylaminopropyloxyimino)]-cyclohexane (compound G);

2-[(Z)-phenylmethylene]-1-[(E)-2-diisopropylaminoethoxyimino)]-cycloheptane (compound H);

2-[(E)-phenylmethylene]-1-[(E)-(3-dimethylaminopropyloxyimino)]-cyclooctane (compound I);

2-[(E)-phenylmethylene]-1-[(E)-(2-isopropylaminoethoxyimino)]-cyclohexane (compound K);

2-[(E)-phenylmethylene]-1-[(Z)-(2-diisopropylaminoethoxyimino)]-cyclohexane (compound L).

Pharmaceutically acceptable acid addition salts of compounds of formula (I) may be those formed with inorganic and organic acids, e.g. hydrogen chloride, hydrogen bromide, sulfuric, phosphoric, acetic, propionic, methanesulfonic, p-toluolsulfonic, tartaric, succinic, maleinic, fumaric, citric, malic or lactic acid, generally used in the pharmaceutical practice.

Antianginal effects of compounds of the formula (I) were tested by using the method of Nieschulz E., Popendiker, K. and Hofmann I. (Arzneimittelforschung, 5, 680; 1955).

The test compounds were intravenously administered to rats. The results obtained were summarized in Table I:

TABLE I

| Tested compound | Dose, mg/kg | Activity % |
| --- | --- | --- |
| compound A | 2 | 81.5 |
| compound B | 2 | 43.6 |
| compound C | 4 | 80.3 |
| compound D | 0.5 | 47.5 |
| compound E | 2 | 59.5 |
| compound F | 0.5 | 72.0 |
| compound G | 0.5 | 57.0 |
| compound H | 2 | 41.3 |

TABLE I-continued

| Tested compound | Dose, mg/kg | Activity % |
|---|---|---|
| compound I | 2 | 84.0 |
| compound K | 2 | 32.5 |
| compound L | 4 | 87.0 |
|  | 1 | 38.0 |
| Prenylamine | 1 | 23.0 |
|  | 2 | 32.0 |
|  | 4 | 42.0 |

The data tabulated above show that compounds of general formula (I) exhibit an equal or even multiple enhanced activity, compared to Prenylamine (N-3,3-diphenylpropyl-1-methylphenyl-ethylamine) in respect of the said test.

The most active derivatives of the compounds of general formula (I) have much higher therapeutic indices than Prenylamine used as reference. The respective figures are shown in Table II below.

TABLE II

| Tested compound | $LD_{50}$ mg/kg iv. | $ED_{50}$ mg/kg iv. | Therapeutic index |
|---|---|---|---|
| compound G | 12.5 | 0.38 | 32.90 |
| compound F | 42.0 | 0.35 | 120.00 |
| compound D | 40.0 | 0.52 | 76.90 |
| Prenylamine | 11.5 | 6.50 | 1.77 |

For oral administration, tablets, dragées, intestinosolvent pills or dragées, or capsules may be prepared. They contain 10 to 100 mg. of active ingredient per unit dose.

Preferably, tablets containing 25 mg., dragées of 50 mg. or capsules of 25 mg. of active ingredient, respectively, further injectable solutions with a concentration of 25 mg. of active ingredient per milliliter can be prepared.

Pharmaceutical preparations for oral administration (tablets, dragées or capsules) may contain carriers and auxiliary substances, for example sodium citrate, calcium carbonate, calcium phosphate, starches, such as potato, maize, or carboxymethylated starch, silicic acid, or binders, such as polyvinyl pyrrolidone, gelatine, etc. Tablet formulations can further be complemented with lubricants, for example with magnesium stearate, talc, or sodium dodecylsulfate. When preparing aqueous suspensions and/or elixirs, the active ingredient may be mixed with several kinds of flavoring substances, dyestuffs, emulsifiers, wetting agents and/or diluents, such as water, ethanol, propylene glycol, glycerol, etc.

Tablets may be manufactured by dry or wet granulation procedure. When preparing dragées, the dragée kernels can be provided with an appropriate coating in a manner known per se. In case of capsules, the suitably prepared preblended mixture of components may be filled into hard or soft gelatine capsules.

Suppositories for rectal administration may contain 25 to 100 mg. of active ingredient. In these formulations the active compounds of general formula (I), having antianginal acitivity, may be complemented with sedatives. When so, the rectal suppository may contain not more than 50 mg. of active compound of general formula (I). Preparation of said suppository formulations can be carried out in such a way that after evenly dispersing the active ingredient in the molten vehicle of the formulation (e.g. in cocoabutter) the dispersion is chilled, filled into forms, and the ready wares are wrapped into tinfoil.

Injections for parenteral use may be administered intravenously, intramuscularly, intraperitoneally or subcutaneously. The injectable solutions contain 5 to 50 milligrams of active ingredient per milliliter, preferably 25 mg./ml. It is advantageous to make use of ampoules of 2 ml. capacity in the practice; hence, the active ingredient content of the ampoules will generally range from 10 to 100 mg./ampoule. The injectable solutions for parenteral use may contain diluents, for example sesame oil, peanut oil, aqueous propylene glycol, or pharmaceutically acceptable organic solvents or, preferably, water. The aqueous solutions may, if desired, be buffered in a known manner, or the osmolality of the liquid diluents may be adjusted to isotonic by adding appropriate amounts of sodium chloride or glucose. The prepared solutions can, if desired, be sterilized by methods usually applied in the practice.

The pharmaceutical compositions having antianginal activity, prepared according to the present invention, can generally be administered in daily doses from 0.25 mg. to 40 mg. per kg. of body weight. The preferred dose ranges from 1 to 20 mg. per kg. of body weight. The daily regime of delivery comprises one to three administrations a day. The proper choice of the dose to be administered — depending upon the activity of the active substance used, the mode of administering of the drug, the physical status of the patient, and other factors—should always rely upon the doctor's prescription.

SPECIFIC EXAMPLES

The invention is elucidated in detail by the aid of the following non-limiting formulational Examples.

EXAMPLE 1

The composition of tablets is as follows:

| active ingredient [compound of formula (I)] | 25.0 mg. |
|---|---|
| maize starch | 97.0 mg. |
| polyvinyl pyrrolidone | 175.0 mg. |
| magnesium stearate | 3.0 mg. |
|  | 300.0 mg. |

The active ingredient and the maize starch are humidified by an aqueous polyvinyl pyrrolidone solution of approx. 15% w/v., followed by granulation, and drying of the wet granules at about 40°–45° C. The dried granulate is thoroughly mixed with magnesium stearate, and the mixture so obtained is further processed by a tablet machine, equipped with an appropriate pressing tool, to give tablets of 300 mg. weight containing 25 mg. of active ingredient. One manufacturing lot includes 1000 tablets.

EXAMPLE 2

Dragées of the following composition are prepared:

| active ingredient [compound of formula (I)] | 50.0 mg. |
|---|---|
| lactose | 94.0 mg. |
| polyvinyl pyrrolidone | 4.0 mg. |
| magnesium stearate | 2.0 mg. |
|  | 300 mg. |

Granulates are prepared according to Example 1, and from them dragée kernels of 150 mg. weight are pressed. The dragée kernels are coated with a layer containing sugar and talc in a manner known per se, followed by colouring with an approved food colorant and polishing with bee wax.

EXAMPLE 3

25 mg. of active ingredient of formula (I) are dissolved in 1000 ml. of distilled water. The solution is filled into 500 ampoules. In this way ampoules containing 2 ml. of a solution containing 25 mg./ml. of active agent each are obtained.

EXAMPLE 4

Gelatine capsules of the following composition are prepared:

| | |
|---|---|
| active ingredient [compound of formula (I)] | 25.0 mg. |
| maize starch | 122.0 mg. |
| colloidal silica | 3.0 mg. |
| | 150.0 mg. |

The ingredients are homogenized, and the homogenate is filled into hard gelatine capsules. 1000 pieces of capsules of 150 mg. (filling) weight each, containing 25.0 mg. of active ingredient per capsule, make a lot.

What we claim is:

1. A method of treating angina in an animal subject suffering therefrom which comprises administering to said animal subject a therapeutically effective amount of a compound of formula (I)

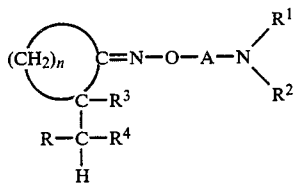

wherein $n=4$, 5 or 6, and if $n=4$, then ($A_1$)
$R^3$ and $R^4$ together form a chemical bond,
R is phenyl,
A is trimethylene,
$R^1$ and $R^2$ are each a methyl group, and the molecule has an (E, Z) configuration; or ($A_2$)
$R^3$ and $R^4$ together form a chemical bond,
R is 4-chlorophenyl,
A is ethylene,
$R^1$ is isopropyl,
$R^2$ is hydrogen, and the molecule has an (E, E) configuration; or ($A_3$)
$R^3$ and $R^4$ together form a chemical bond,
R is 4-chlorophenyl,
A is trimethylene,
$R^1$ and $R^2$ are each an isopropyl group, and the molecule has an (E, E) configuration; or ($A_4$)
$R^3$ and $R^4$ together form a chemical bond,
R is phenyl,
$A_1$ is trimethylene,
$R^1$ and $R^2$ are each an isopropyl group, and the molecule has an (E, E) configuration; or ($A_5$)
$R^3$ and $R^4$ together form a chemical bond,
R is phenyl,
A is ethylene,
$R^1$ is isopropyl,
$R^2$ is hydrogen, and the molecule has an (E, E) configuration; or ($A_6$)
$R^3$ and $R^4$ together form a chemical bond,
R is phenyl,
A is ethylene,
$R^1$ and $R^2$ are each an isopropyl group, and the molecule has an (E, E) configuration; or if $n=5$, then ($B_1$)
$R^3$ and $R^4$ together form a chemical bond,
R is phenyl,
A is ethylene,
$R^1$ and $R^2$ are each a methyl group, and the molecule has a (Z, E) configuration; or ($B_2$)
$R^3$ and $R^4$ are each hydrogen,
R is phenyl,
A is ethylene,
$R^1$ and $R^2$ are each a methyl group, and the molecule has an (E, E) configuration; or ($B_3$)
$R^3$ and $R^4$ together form a chemical bond,
R is phenyl,
A is ethylene,
$R^1$ and $R^2$ are each a methyl group, and the molecule has an (E, E) configuration; or ($B_4$)
$R^3$ and $R^4$ together form a chemical bond,
R is phenyl,
A is ethylene,
$R^1$ and $R^2$ are each an isopropyl group, and the molecule has a (Z, E) configuration; or if $n=6$, then (C)
$R^3$ and $R^4$ together form a chemical bond,
R is phenyl,
A is trimethylene,
$R^1$ and $R^2$ are each a methyl group, and the molecule has an (E, E) configuration, or a pharmaceutically acceptable acid addition salt thereof.

2. The method defined in claim 1 wherein said compound is selected from the group which consists of:
  2-[(E)-phenylmethylene]-1-[(Z)-(3-dimethylaminopropyloxyimino)]-cyclohexane;
  2-[(Z)-phenylmethylene]-1-[(E)-(2-dimethylaminoethoxyimino)]-cycloheptane;
  2-[(E)-(4-chlorophenyl)-methylene]-1-[(E)-(2-isopropylamino-ethoxyimino)]-cyclohexane;
  2-benzyl-1-[(E)-(2-dimethylaminoethoxyimino)]-cycloheptane;
  2-[(E)-phenylmethylene]-(E)-(2-dimethylaminoethoxyimino)]-cycloheptane;
  2-[(E)-(4-chlorophenyl)-methylene]-1-[(E)-(3-diisopropylamino)-propyloxyimino]-cyclohexane;
  2-[(E)-phenylmethylene]-1-[(E)-(3-diisopropylaminopropyloxyimino)]-cyclohexane;
  2-[(Z)-phenylmethylene]-1-[(E)-2-diisopropylaminoethoxyimino)]-cycloheptane;
  2-[(E)-phenylmethylene]-1-(E)-(3-dimethylaminopropyloxyimino)]-cyclooctane;

2-[(E)-phenylmethylene]-1-(E)-(2-isopropylaminoe-
thoxyimino)]-cyclohexane; and
2-[(E)-phenylmethylene]-1-1-[(Z)-(2-diiso-
propylaminoethoxyimino)]-cyclohexane, or a pharmaceutically acceptable acid addition salt thereof.

3. The method defined in claim 2 wherein said compound is 2-[(E)-(4-chlorophenyl)-methylene]-1-[(E)-(3-dissopropylamino)-propyloxyimino)]-cyclohexane.

4. The method defined in claim 2 wherein said compound is 2-benzyl-1-[(E)-(2-dimethylamino-ethoxyimino)]-cycloheptane.

5. The method defined in claim 1 wherein said compound is administered orally or parenterally.

6. The method defined in claim 2 wherein said compound is administered orally or parenterally.

* * * * *